US006155498A

United States Patent [19]

Yamamoto

[11] Patent Number: 6,155,498

[45] Date of Patent: Dec. 5, 2000

[54] SPRAYER

[75] Inventor: Kenzo Yamamoto, Wakayama, Japan

[73] Assignee: Yamaho Industrial Co., Ltd., Wakayama, Japan

[21] Appl. No.: 09/431,090

[22] Filed: Nov. 1, 1999

[30] Foreign Application Priority Data

Nov. 2, 1998 [JP] Japan ................................. 10-312278

[51] Int. Cl.[7] .................................................... A61M 11/02

[52] U.S. Cl. .......................... 239/373; 239/337; 222/401

[58] Field of Search .................................... 239/337, 373, 239/320, 321, 322, 152; 222/401, 402, 189.06; 137/209, 202

[56] References Cited

U.S. PATENT DOCUMENTS

| | | | |
|---|---|---|---|
| 2,772,921 | 12/1956 | Nance | 239/337 |
| 3,265,308 | 8/1966 | Hopkins | 239/373 |
| 4,893,751 | 1/1990 | Armstrong | 239/150 |
| 5,221,026 | 6/1993 | Williams | 222/401 |

FOREIGN PATENT DOCUMENTS

| | | |
|---|---|---|
| 682213 | 5/1930 | France . |
| 702504 | 4/1931 | France . |
| 808183 | 1/1937 | France . |
| 931964 | 3/1948 | France . |

*Primary Examiner*—Andres Kashnikow
*Assistant Examiner*—Lisa Ann Douglas
*Attorney, Agent, or Firm*—Wenderoth, Lind & Ponack, L.L.P.

[57] ABSTRACT

A sprayer can convert the entire manual effort used to operate a manual pump into energy for spraying liquid. The sprayer has a liquid tank filled with a liquid, and an air tank having a pressurized air supply valve through which pressurized air can be introduced into the air tank. The air tank communicates with a float valve having a valve hole communicating with a spray nozzle and a hollow rod as the outlet of a manual pump. Pressurized air is introduced into the air tank through the pressurized air supply valve to increase the air pressure in the tank to a predetermined bias pressure. Then, the manual pump is operated to suck liquid in the liquid tank and supply the thus sucked liquid through the float valve into the air tank.

5 Claims, 8 Drawing Sheets

SPRAYER

BACKGROUND OF THE INVENTION

This invention relates to a sprayer, particularly a manual atomizer.

A conventional manual sprayer has a liquid tank filled with a liquid and a manual pump having a lever. By manually operating the lever, pressurized air is supplied into the liquid tank, so that the air pressure in the tank increases. When the pressure in the tank has increased sufficiently, an on-off valve for the spray nozzle is opened to spray liquid in the tank through a nozzle under the air pressure in the tank.

As liquid is discharged, the air pressure in the tank decreases. When the air pressure drops below a predetermined level, it is impossible to spray liquid with sufficient momentum any more. Thus, before the air pressure drops below the predetermined level, the manual lever has to be operated again to reincrease the air pressure.

That is to say, not all the air pressure supplied by operating the handle lever at the beginning of use is used for spraying. Thus when the pressure drops below a predetermined value, it is necessary to increase the pressure again by operating the handle lever. After use, the air pressure below this pressure is released into the atmosphere. After all, part of the air pressure fed by operating the handle lever is not used as spraying energy, so that the efficiency of the pump is bad.

An object of the invention is to provide a sprayer which can convert the entire manual energy used to operate the manual pump into energy for spraying of liquid.

SUMMARY OF THE INVENTION

According to this invention, there is provided a sprayer comprising an air tank having a liquid inlet through which liquid is introduced and discharged and a pressurized air inlet through which pressurized air is introduced into the air tank, a float valve having a float chamber communicating with the air tank and formed with a valve hole, and a valve body adapted to be pressed against the valve hole to close the float valve under air pressure applied from the air tank to the float chamber and to float up and separate from the valve hole to open the float valve when liquid is supplied from the air tank to the float valve, the float valve having a liquid inlet port through which liquid is supplied into the float chamber through the valve hole, and a nozzle having an on-off valve and communicating with the liquid inlet port and the valve hole.

Other features and objects of the present invention will become apparent from the following description made with reference to the accompanying drawings, in which:

DETAILED DESCRIPTION OF THE PREFERRED EMBODIMENTS

Figure 1:
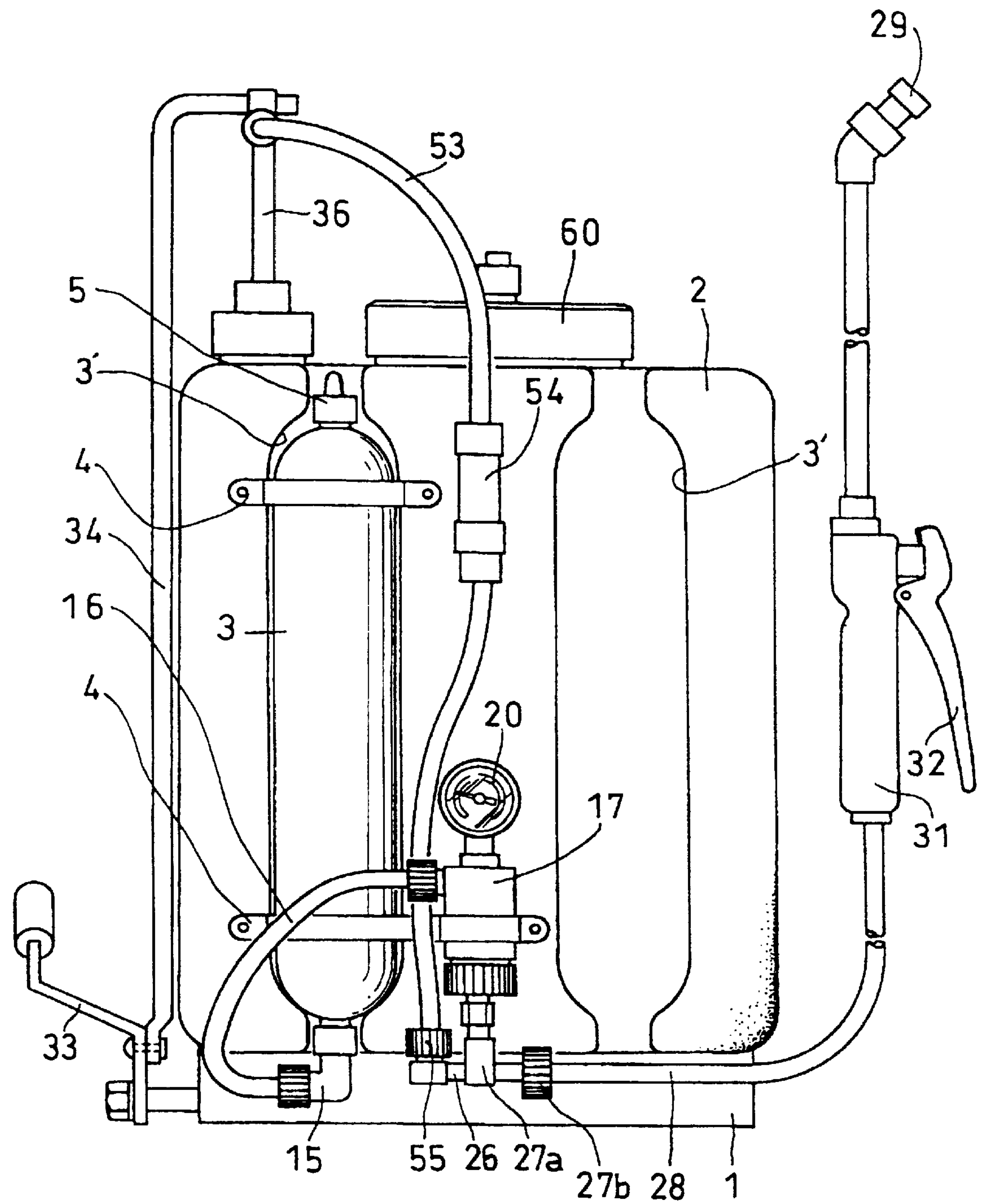
FIG. 1 is a front view of a sprayer embodying the invention.
Figure 2:
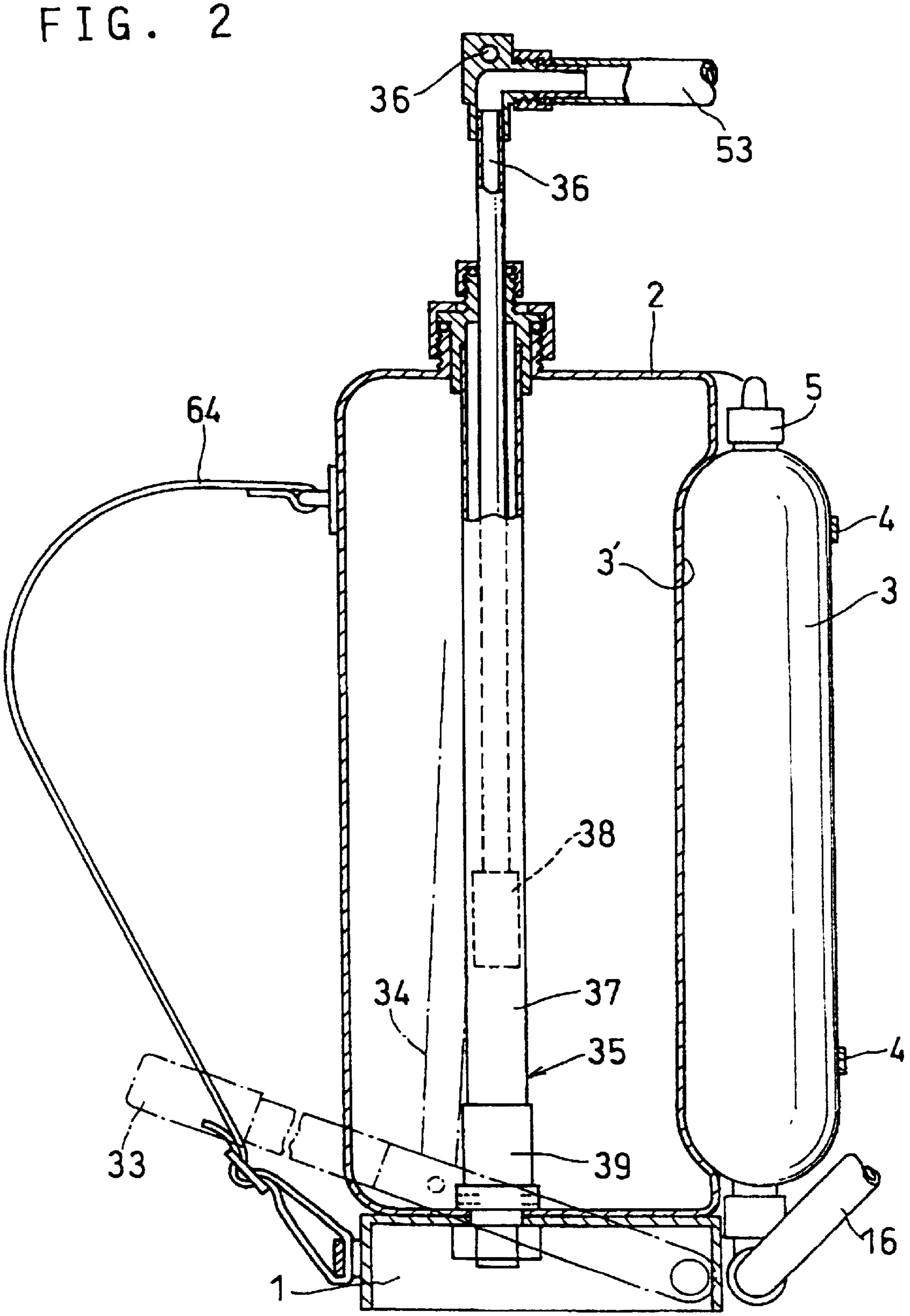
FIG. 2 is a side view in vertical section of the same.

FIGS. 1 and 2 show a sprayer embodying this invention. The sprayer shown is a manual atomizer having a liquid tank 2 mounted on a support plate 1 and formed with two recesses 3' in back thereof to receive air tanks.

In the illustrated embodiment, an air tank 3 is set in one of the two recesses 3' by brackets 4. If greater air supply is needed, an extra air tank is set in the other recess 3'.

Figure 3B:
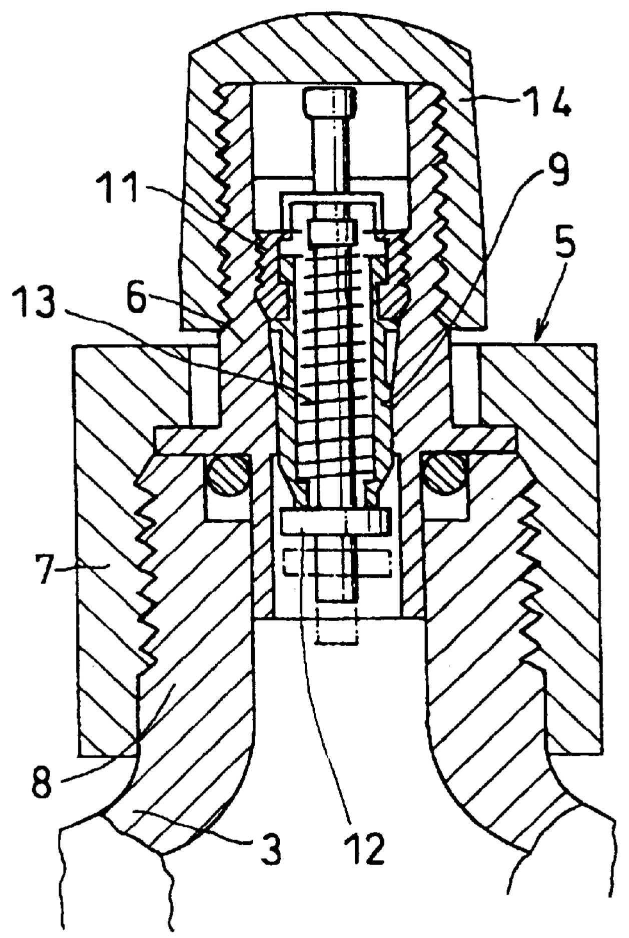
FIG. 3B is a partially enlarged sectional view of FIG. 3A.
Figure 3A:
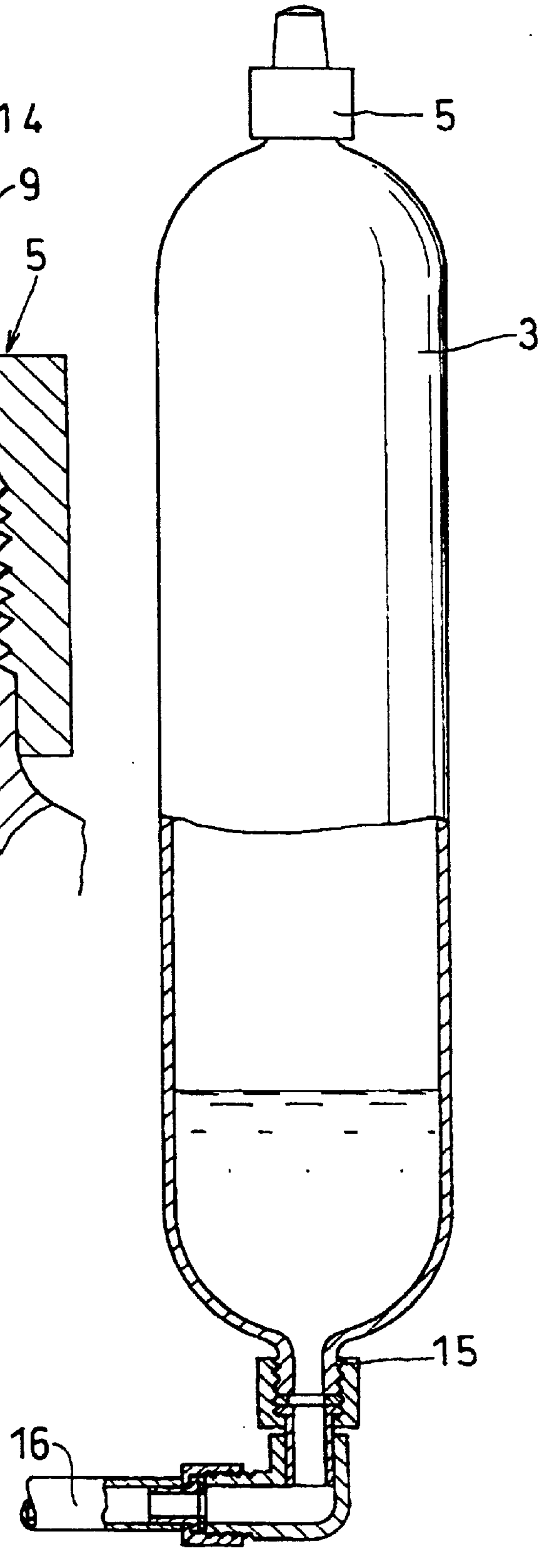
FIG. 3A is a partially omitted sectional view of an air pump of the same.

At the top end of the air tank 3, a pressurized air supply valve 5 is provided. As shown in FIG. 3, the valve 5 includes a valve chest 6 secured to the top end 8 of the tank by a nut 7, and a valve seat 9 fixedly mounted in the valve chest 6 by a fixing member 11. A valve body 12 has a shaft portion extending through the valve seat 9 and is pressed against the bottom end of the valve seat 9 by a coil spring 13 mounted around the shaft portion to keep it normally closed.

In the closed state, the top end of the shaft of the valve body 12 almost abuts the top wall of the valve chest 6 and a cap 14 closes the top opening of the valve chest 6.

To supply pressurized air into the tank 3, the cap 14 is removed, and an outlet port of an air compressor or manual air pump is connected to the top of the valve chest 6 to introduce pressurized air into the valve chest. Under the air pressure from the air compressor, the valve body 12 is pushed down and pressurized air is fed into the tank. As soon as the feed of pressurized air stops, the coil spring 13 pushes the valve body 12 back to the closed position.

A first hose 16 is connected to the bottom end 15 of the air tank 3 and the other end of the first hose is connected to a float valve 17.

Figure 4B:
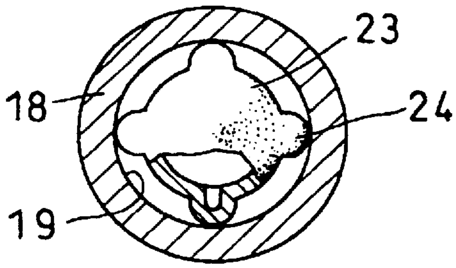
FIG. 4B is a partial section of FIG. 4A.
Figure 4A:
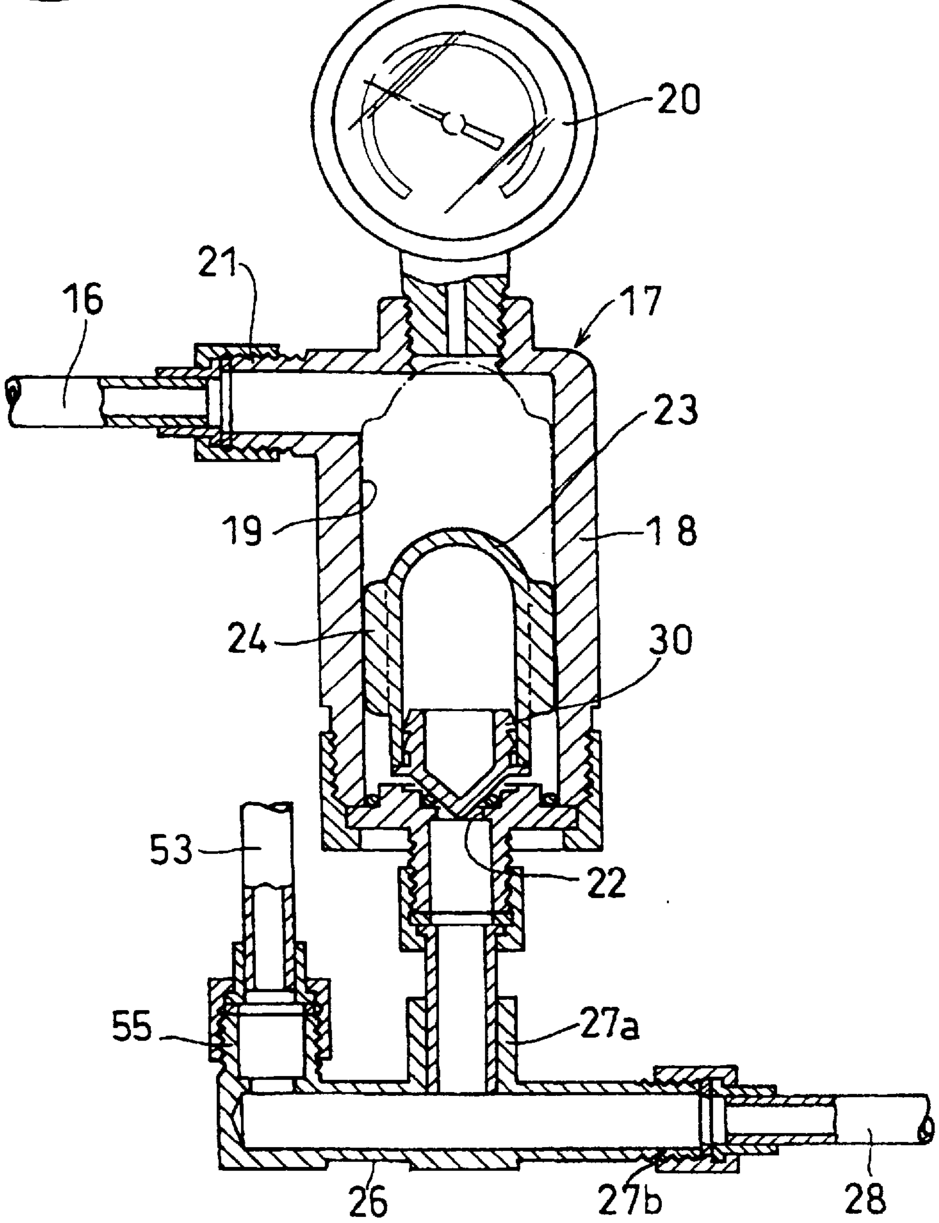
FIG. 4A is a sectional view of a float valve of the sprayer of FIG. 1.

As shown in FIGS. 4A and 4B, the float valve 17 includes a valve case 18 defining a float chamber 19 and formed with a liquid outlet port 21 to which is connected the first hose 16. A liquid inlet port 22 is formed at the bottom end of the valve case 18.

In the float chamber 19, a valve body 30 having a float 23 is mounted. The float 23 is guided by several ribs 24 formed on its outer periphery so as to be vertically slidable. When pressurized air is supplied into the float chamber 19, the valve body 30 closes the port 22 by seating on its edge. Conversely, if liquid is supplied, the float 23 floats up in the liquid supplied, so that the valve body 30 separates from the port 22, thus opening the port.

The outlet port 22 is connected to one branch 27*a* of a branch pipe 26. The pipe 26 has another branch 27*b* connected to a second hose 28 which is connected to a grip 31 of a spray nozzle 29 (FIG. 1). By operating a lever 32 mounted on the grip, a cock (not shown but provided inside the grip) is opened and closed for fluid communication between the spray nozzle 29 and the hose 28.

A pressure gauge 20 for measuring the pressure in the float chamber 19 is mounted on the valve case 18.

As shown in FIGS. 1 and 2, a handle lever 33 is pivotably mounted to one side of the support plate 1. To an intermediate portion of the lever 33, the bottom end of a link 34 is pivotably connected. The link 34 has its top bent in the shape of an inverted L and pivotably coupled to a hollow rod 36 of a manual pump 35 (FIG. 2). The manual pump 35 has a cylinder 37 supported upright on the inner bottom of the liquid tank 2 through a valve chest 39. A piston 38 is inserted in the cylinder 37 and the hollow rod 36 is coupled to the piston 38.

Figure 5:
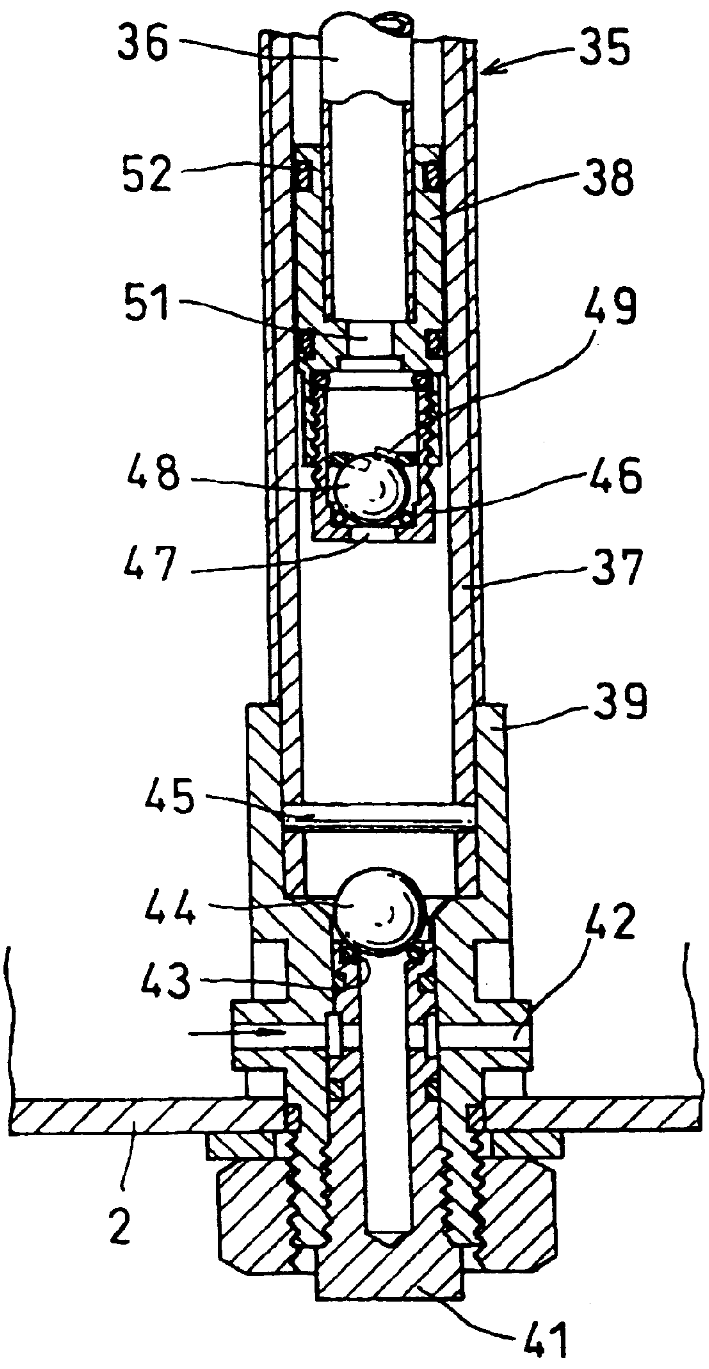
FIG. 5 is a sectional view of a manual pump of the sprayer of FIG. 1.

Referring now to FIG. 5, the valve chest 39 is fixed to the bottom of the cylinder 37. A valve seat member 41 is threaded into the valve chest 39. A passage 42 extends through the valve chest 39 and the valve seat member 41 and communicates with the interior of the liquid tank 2. Formed in the top end of the valve seat member 41 is a valve hole 43 communicating with the passage 42. A spherical valve body 44 rests on the hole 43, closing the hole by its own weight.

A horizontal bar 45 is provided over the valve body 44 to limit its upper movement.

A valve chest 46 is threaded into the bottom end of the piston 38. A check valve 48 in the form of a spherical ball seats on the edge of a hole 47 formed in the bottom wall of the valve chest 46 to close the hole 47. A spring washer 49 rests on the check valve 48 to prevent a passage 51 connecting the interior of the valve chest 46 and the interior of the hollow rod 36 from being closed by the check valve 48 when the latter is pushed up. A piston ring 52 is mounted around the piston 38.

Referring back to FIGS. 1 and 2, a third hose 53 is connected to the top end of the hollow rod 36. A filter 54 is provided in the hose 53, which is connected to a liquid supply port 55 of the branch pipe 26 (FIG. 4A). The supply port 55 is connected to the float valve 17 through the branch 27*a* and to the second hose 28 (see also FIG. 4A).

Figure 6:
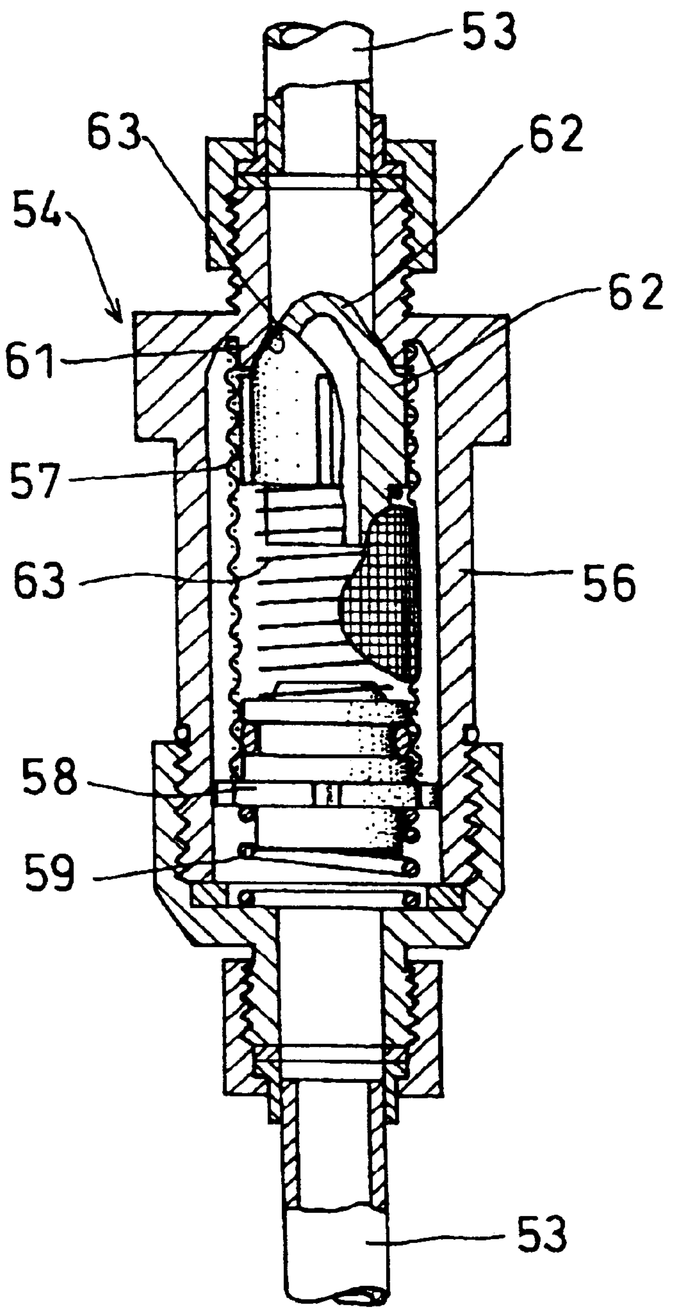
FIG. 6 is a sectional view of a filter of the sprayer of FIG. 1.

As shown in FIG. 6, the filter 54 comprises a tubular filter case 56, a filter element 57 in the form of a cylindrical net mounted in the case 56, a support member 58 supporting the lower end of the filter element 57, and a spring 59 biasing the filter element 57 upwardly against a mounting portion 61.

A valve body 62 is mounted in the filter element 57. A relatively weak spring 63 is mounted between the valve body 62 and the support member 58 to keep the valve body 62 pressed against the edge of a valve hole 63 formed in the mounting portion 62 to close the hole 63.

Now the operation is described. Before use, a required liquid is poured into the tank 2 by removing the lid 60 (FIG. 1). After putting on the lid 60, a nozzle of an air compressor is connected to the pressurized air supply valve 5 of the air tank 3 to supply pressurized air into the air tank to increase the pressure in the tank to a predetermined level, which has to be so low as to be possible to supply a predetermined amount of liquid into the air tank 3 by manual operation of the manual pump 35. This initial pressure in the air tank is hereinafter referred to as "bias pressure".

The bias pressure is applied through the first hose 16 to the float valve 17, and pushes down the valve body 30 (FIG. 4A), closing the valve hole 22. Thus, the bias pressure in the air tank 3 is maintained. The bias pressure is indicated on the pressure gauge 20.

When this preparation is complete, the sprayer is carried on the back of an operator using a strap 64 (FIG. 2), and the operator moves the handle lever 33 of the pump 35 up and down to reciprocate the hollow rod 36 and piston 38.

Referring to FIG. 5, suppose that the piston 38 is rising. As the piston rises, a negative pressure produced in the cylinder 37 pulls up the valve body 44, opening the valve hole 43. Liquid in the tank 2 is thus sucked through the passage 42 into the cylinder 37.

When the piston subsequently begins to descend, the valve body 44 is pushed down to close the hole 43, while the valve body 48 in the piston 38 opens the valve hole 47. Thus, the liquid in the cylinder 37 is compressed by the piston 38 and flows through the hollow rod 36, third hose 53, filter 54, inlet port 55 of the branch pipe 26, its branch 27*a* into the float valve 17.

Once in the float valve 17 (FIG. 4A), liquid pushes up the valve body 30, enters the float chamber 19, passes the gap around the float 23, and flows through the outlet 21 and first hose 16 into the air tank 3. The air pressure in the air tank thus increases. Liquid may be supplied until the air pressure in the air tank rises to such a level that the handle bar 33 is not movable any further.

When the pressure in the air tank has increased sufficiently, the cock in the grip 31 is opened by operating the lever 32 to spray liquid in the air tank 3 through the spray nozzle 29. By opening the cock, liquid in the tank 3 flows under pressure through the first hose 16, float valve 17, branch 27*b* of the branch pipe 26 and second hose 28 and is discharged through the nozzle 29. Since the liquid pressure keeps the check valve 48 closed, liquid will never flow back into the liquid tank 2 through the third hose 53.

As spraying proceeds and liquid is discharged, and when the pressure in the air tank 3 decreases to the bias pressure, the handle lever 33 is operated again with the cock in the grip 31 open or closed to resupply liquid into the air tank 3. Thereafter spraying may be continued in the same manner as described above.

Two air tanks may be used instead of one as shown.

Figure 7:
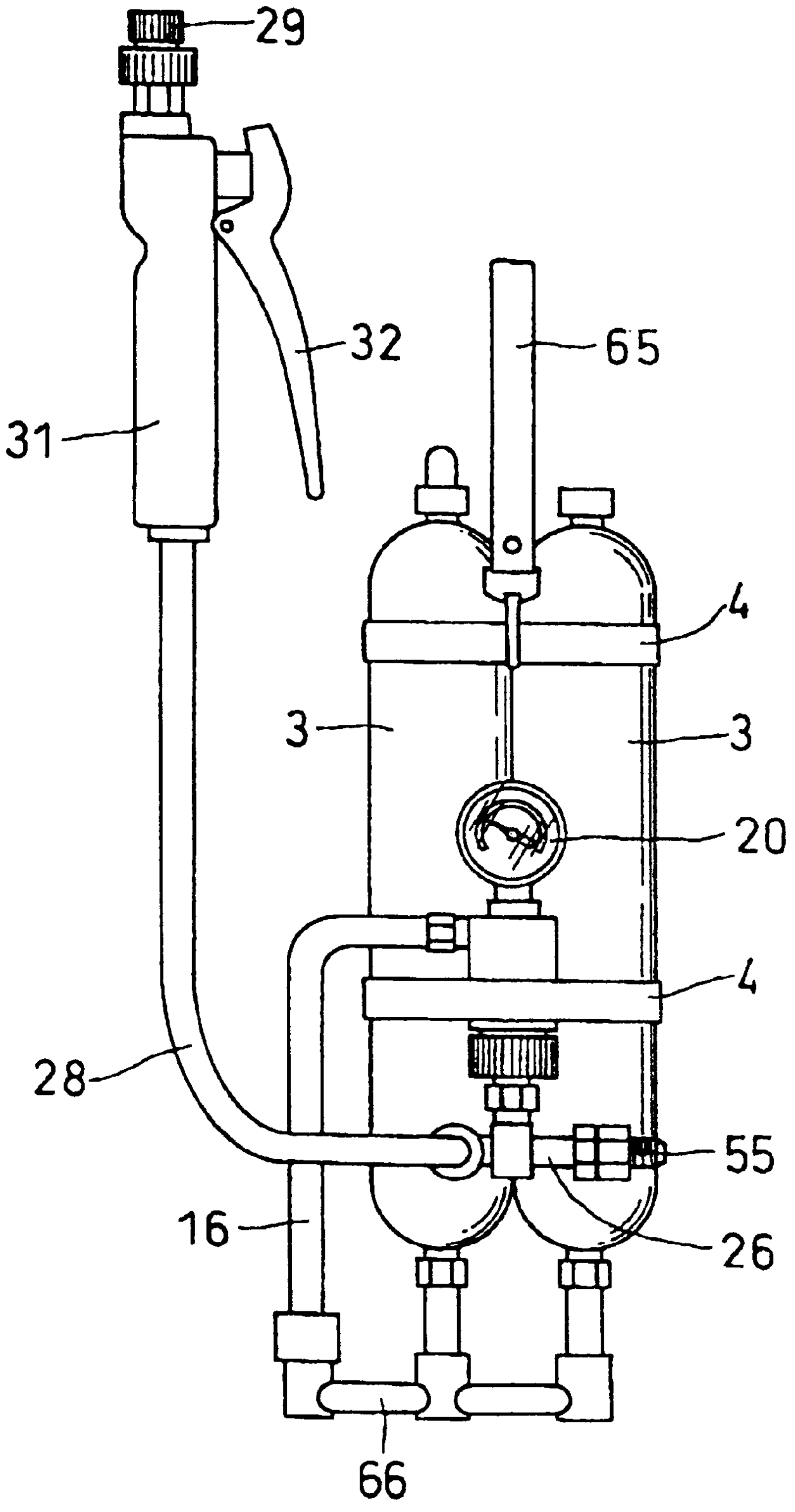
FIG. 7 is a front view of another embodiment.
Figure 8:
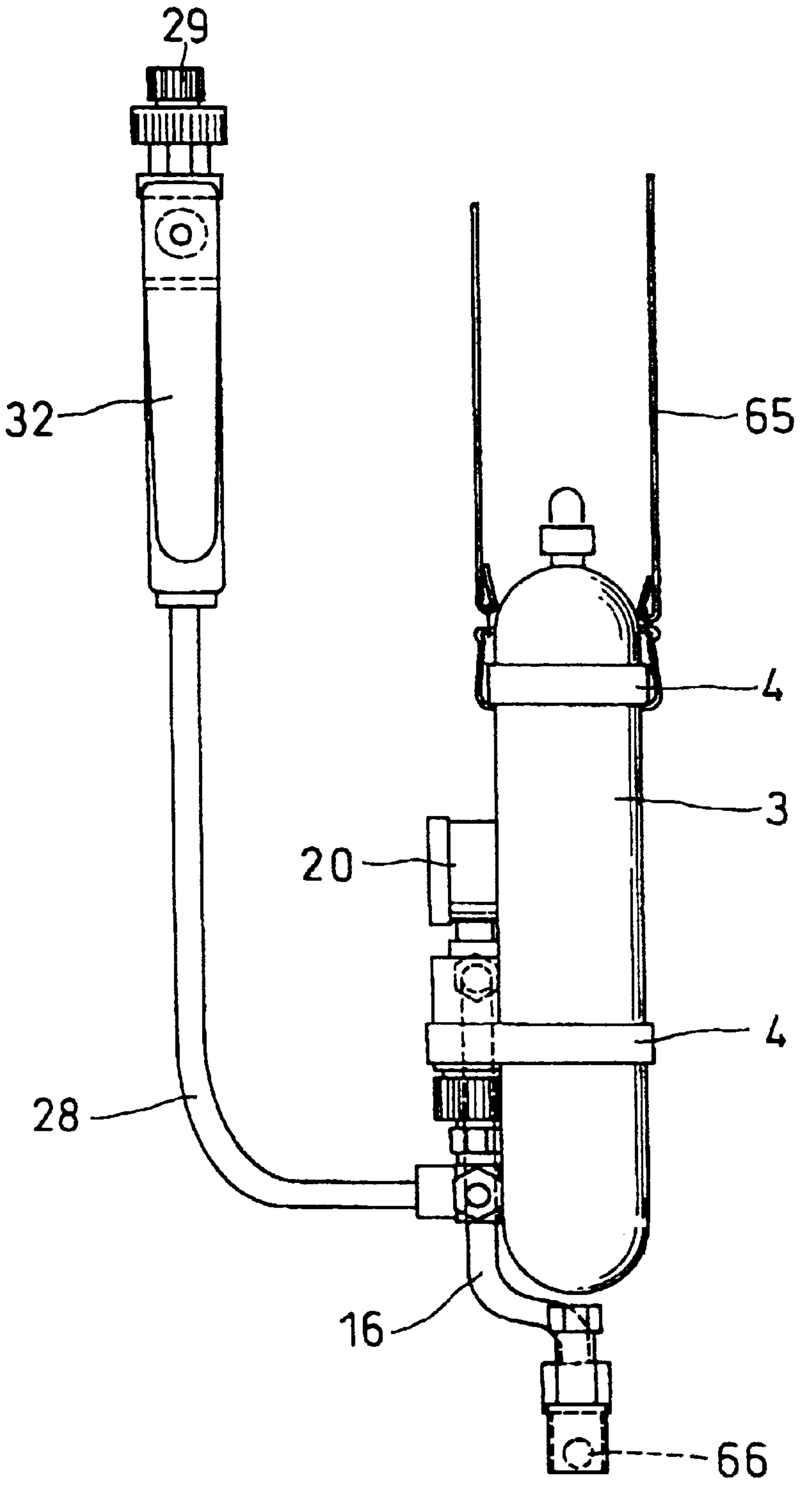
FIG. 8 is a partial side view of the same.

FIGS. 7 and 8 show another embodiment of the invention, which mainly differs from the first embodiment in that it has no support member 1, liquid tank 2, manual pump 35 and third hose 53, and that two air tanks 3 are coupled together by brackets 4. A carrying strap 65 is fastened to one of the brackets. At their bottoms, the air tanks communicate with each other through a pipe 66. The liquid inlet port 55 of the branch pipe 26 is closed by a normally closed valve and forms a joint to which an outlet port of a separate liquid injector pump is detachably connected. A pressurized air supply port 5 is provided at the top end of one of the air tanks 3. Otherwise, this embodiment is the same as the first embodiment.

In this embodiment, liquid is supplied into the air tanks from the separate liquid injector pump. After charging liquid, the injector pump is disconnected from the sprayer, and the sprayer alone is carried on the shoulder of an operator for use. One of the air tanks may be omitted.

Since the air pressure in the air tank is controlled so that the pressure therein will not decrease below a predetermined bias pressure, liquid that has been supplied into the air tank by operating the handle lever can be entirely discharged under a pressure above the predetermined pressure. In other words, the pressure increased in the air tank by operating the handle lever is used entirely for the discharge of liquid. Thus energy efficiency is high.

What is claimed is:

1. A sprayer comprising an air tank having a liquid inlet through which liquid is introduced and discharged and a pressurized air inlet through which pressurized air is introduced into said air tank, a float valve having a float chamber communicating with said air tank and formed with a valve hole, and a valve body adapted to be pressed against said valve hole to close said float valve under air pressure applied from said air tank to said float chamber and to float up and separate from said valve hole to open said float valve when liquid is supplied from said air tank to said float valve, said float valve having a liquid inlet port through which liquid is supplied into said float chamber through said valve hole, and a nozzle having an on-off valve and communicating with said liquid inlet port and said valve hole.

2. The sprayer as claimed in claim 1 wherein said pressurized air inlet includes a check valve that permits a flow of pressurized air into said air tank and prevents said flow out of said air tank.

3. The sprayer as claimed in claim 2 further comprising a liquid tank, and a manual pump mounted in said liquid tank and having an inlet port for sucking liquid in said liquid tank and an outlet port for supplying the thus sucked liquid to said liquid inlet port of said float valve.

4. The sprayer as claimed in claim 1 further comprising a liquid tank, and a manual pump mounted in said liquid tank and having an inlet port for sucking liquid in said liquid tank and an outlet port for supplying the thus sucked liquid to said liquid inlet port of said float valve.

5. The sprayer as claimed in claim 4 wherein the outlet port of said manual pump is connected to said liquid inlet port through a filter and a check valve that permits a flow of liquid from said manual pump to said liquid inlet port and prevents the flow in a reverse direction.

* * * * *